United States Patent [19]
Richardson

[11] Patent Number: 5,679,651
[45] Date of Patent: Oct. 21, 1997

[54] TREATMENT FOR SYSTEMIC LUPUS ERYTHEMATOSUS

[76] Inventor: Bruce C. Richardson, 3400 West Bayshore Rd., Palo Alto, Calif. 94303

[21] Appl. No.: 461,391

[22] Filed: Jun. 5, 1995

[51] Int. Cl.$^6$ .................................................. A61K 31/70
[52] U.S. Cl. ........................................................ 514/49
[58] Field of Search .................................................. 514/49

[56] References Cited

PUBLICATIONS

Yung, et al., *Rheum. Dis. Clin. North Am.*, 20:61 (1994).
Decker, et al., *Ann. Intern. Med.*, 91:587 (1979).
Quddus, et al., *J. Clin. Invest.* 92:38 (1993).
Yung, et al., *J. Immunol.*, 154:3025–3035 (1995).
Nyce, et al. (*Nucleic Acids Research*, 14(10):4353–4367 (1986).
*Physicians' Desk Reference*, 48th Edition, (Medical Economics Data Production Co., Montvale, NJ), 2405–2407 (1994).
Richardson, et al., *Arthritis and Rheumatism*, 35(6):647–62 (1992).
Richardson, et al., *Arthritis and Rheumatism*, 33(11):1665–73 (1990).
Krupp, et al., *Ann. Neurol.*, 17(4):344–9 (1985).
Harris, et al., *Int. J. Radiat. Biol. Relat. Stud. Phys. Chem Med.*, 47(6):689–99 (1985).
Kurki, et al., *Exp. Cell Res.*, 166(1):209–19 (1986).
Bayliss, et al., *Clin Exp. Rheumatol.*, 10:420–421 (1992).

*Primary Examiner*—James H. Reamer
*Attorney, Agent, or Firm*—David A. Lowin

[57] ABSTRACT

Cytarabine (ara-C) is effective in the treatment of systemic lupus erythematosus.

9 Claims, No Drawings

TREATMENT FOR SYSTEMIC LUPUS ERYTHEMATOSUS

FIELD OF THE INVENTION

The present invention relates to the treatment of disease, particularly to systemic lupus erythematosus, and specifically to a new use of the compound ara-C in the treatment thereof.

BACKGROUND INFORMATION

As discussed in the *Primer on Rheumatic Diseases, Tenth Edition*, [Schumacher, et al., Eds., (The Arthritis Foundation, Atlanta, Ga.), Chapter 11, pp. 100–116 (1993)] systemic lupus erythematosus ("SLE") is an idiopathic disease characterized by antibodies (autoantibodies) against a wide range of autoantigens in the nucleus and cytoplasm of cells, and a constellation of pathologic abnormalities involving the kidney, skin, brain, lungs and other organs. Autoantibodies to double-stranded DNA and an RNA-protein complex termed Sm are found essentially only in SLE patients and are included as serologic criteria in the classification of SLE. SLE is primarily a disease of young women, ages 15 to 40; it affects about 1 in 2,000 individuals and shows a strong familial aggregation. While genetically determined immune abnormalities are implicated in the cause of SLE, the triggering event is suggested to include both exogenous and endogenous factors, likely to be mutagenic in origin. The pathologic findings of SLE are manifested by inflammation, blood vessel abnormalities encompassing both bland vasculopathy and vasculitis, and immune complex deposition.

Although the cause of SLE remains unknown, certain environmental and pharmacologic agents, including UV light and drugs such as procainamide and hydralazine have been shown to trigger a lupus-like illness in genetically predisposed individuals. Yung, et al., *Rheum. Dis. Clin. North Am.*, 20:61 (1994) and Decker, et al., *Ann. Intern. Med.*, 91:587 (1979). Autoreactivity induction by inhibition of T cell DNA methylation, e.g., using the drug 5-azacytidine ("5-aza-C") has also been shown to cause a lupus-like disease in syngenic recipients. Quddus, et al., *J. Clin. Invest.* 92:38 (1993). This has been extended to a murine model involving the adoptive transfer of $CD4^+T$ cells treated with the DNA methylation inhibitors. Yung, et al., *J. Immunol.*, 154:3025–3035 (1995).

Clinical manifestations of SLE include: constitutional*, arthritis*, arthralgia*, skin*, mucous membranes, pleurisy, lung, pericarditis, myocarditis, Raynaud's, thrombophlebitis, vasculitis, renal*, nephrotic syndrome, azotemia, CNS, cytoid bodies, gastrointestinal, pancreatitis, lymphadenopathy and myositis (*indicates the most prevalent manifestations). The most common skin manifestation is the "butterfly" rash, commonly precipitated by exposure to sunlight. Subacute cutaneous lupus erythematosus is a relatively distinct cutaneous, lesion, nonfixed, nonscarring, exacerbating, and remitting, again correlated to sun exposure. Discoid lesions are chronic cutaneous lesions and may occur in the absence of systemic manifestations. Alopecia and mucous membrane lesions are other common features. The most common presentations of SLE include latent lupus (patients presenting one or two classification criteria over a period of years), drug-induced lupus (induced, e.g., by chlorpromazine, methyldopa, hydralazine, procainamide and isoniazid, with typically less severe clinical features), antiphospholipid antibody syndrome, and late stage lupus (typically involving mortality from complications that result from the disease itself or as a consequence of its therapy).

Current treatments involve preventive disease management (e.g., avoiding intense sun exposure) and drug therapies involving agents that suppress inflammation or interfere with immune functions (e.g., with NSAIDs, corticosteroids, antimalarials, methotrexate, diaminodiphenylsulfone, azathioprine, nitrogen mustard alkylating agents, danazol, and investigational therapies with cyclosporin A, immune globulin, plasma exchange and total lymphoid irradiation). Given the many combinations of organ system involvement and the need to address treatment of comorbid conditions accounting for considerable morbidity and mortality, it has remained desired to provide an effective treatment for SLE.

The ability of various pharmaceutical agents to modulate DNA methylation has been described in the literature. Nyce, et al. (*Nucleic Acids Research*, 14(10):4353–4367 (1986) describe the relationship between DNA methylation and gene expression, as studied using drugs capable of inducing DNA hypomethylation (such as 5-aza-C) and others capable of inducing DNA hypermethylation (such as the pharmacologically distinct agents ara-C, hydroxyurea and aphidicolin). It was noted that substantial, dose-dependent DNA methylation is inducible by inhibitors of DNA synthesis with distinct pharmacological sites of action, while other DNA synthesis inhibitors were insufficient to induce DNA hypermethylation at all. Thus, DNA hypermethylation as a mechanism of action remains somewhat unpredictable.

Ara-C (available from Upjohn under the trade name CYTOSAR-U, as well as from several generic drug manufacturers, generically known as cytarabine, the chemical name of which is 4-amino-1-β-D-arabinofuranosyl-2 (1H)-pyrimidinone)is an antineoplastic agent having immunosuppressive action, and is indicated for treatment of leukemia. It is known to be a bone marrow suppressant with a known connection to anemia, leukopenia, thrombocytopenia, megaloblastosis and reduced reticulocytes, as well as viral, bacterial, fungal, parasitic or saprophytic infections. A condition known as cytarabine syndrome has been described as characterized by fever, myalgia, bone pain, occasionally chest pain, maculopulpar rash, conjunctivitis and malaise, usually 6–12 hours after administration. Corticosteroids have been shown to be beneficial in treating or preventing this syndrome. Frequent adverse reactions include anorexia, oral and anal inflammation or ulceration, hepatic dysfunction, and rash (some of which are also associated with SLE). See, *Physicians Desk Reference*, 48th Edition, (Medical Economics Data Production Co., Montvale, N.J.), 2405–2407 (1994). It has not been suggested, and indeed given a side effect profile similar to some SLE symptoms would not be expected, that ara-C may be effective in the treatment of SLE.

Aside from the above-referenced, previously unconnected associations between SLE, DNA methylation and various pharmacologically distinct inhibitors of DNA synthesis, it has until the present invention remained unsuggested and unproven as to whether hypermethylation would be an effective treatment and if so, which if any of several distinct potential DNA hypermethylating agents might prove effective.

SUMMARY OF THE INVENTION

It has surprisingly been demonstrated in human refractory cutaneous lupus patients that ara-C is an effective treatment for SLE. Thus, the present invention is addressed to the treatment of SLE, particularly cutaneous systemic lupus erythematosus, by the administration of an effective amount of ara-C.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "treatment" or "treating" means any treatment of a disease in a mammal, including:

(i) preventing the disease, that is, causing the clinical symptoms of the disease not to develop by administration of a protective composition prior to the induction of the disease;

(ii) suppressing the disease, that is, causing the clinical symptoms of the disease not to develop by administration of a protective composition after the inductive event but prior to the clinical appearance or reappearance of the disease;

(iii) inhibiting the disease, that is, arresting the development of clinical symptoms by administration of a protective composition after their initial appearance; and/or (iv) relieving the disease, that is, causing the regression of clinical symptoms by administration of a protective composition after their initial appearance.

It will be understood that in human medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "treatment," as used herein, is meant to include "prophylaxis."

The term "effective amount" means a dosage sufficient to provide treatment for the disease state being treated. This will vary depending on the patient, the disease and the treatment being effected.

Supply of Compound

As indicated above, ara-C is an approved drug available in finished dosage forms suitable for administration from Upjohn and from various generic manufacturers. Other ara-C formulations and combinations (e.g., as described in U.S. Pat. No. 5,262,174; 5,252,713; 5,087,618; 4,943,367; 4,906,666; 4,542,021; and 4,275,057) can be used in the methods of treatment of the present invention.

Utility, Testing and Administration

General Utility

Ara-C is useful for the treatment of SLE, particularly cutaneous systemic lupus erythematosus, and especially refractory cutaneous systemic lupus erythematosus, perhaps by virtue of its putative activity as a human DNA hypermethylation agent. Ara-C can be used in place of azathioprine in established treatment regimens for SLE and as asteroid sparing agent, e.g., to facilitate use of lower prednisone doses.

Testing

*In vivo* activity for the treatment of SLE may be demonstrated by testing of a compound in one of several strains of inbred mice with inherited lupus-like disease, observing for the appearance of ANA production, immune complex glomerulonephritis, lymphadenopathy, and abnormal B and T cell function mimicking the human situation, in control and treated groups, by a modification of the procedures described in *Primer on Rheumatic Diseases*, at page 104.

Human clinical efficacy is demonstrated in clinical trials, employing methodology known to those skilled in the art, e.g., as described in the Examples.

Administration

Ara-C is administered at a therapeutically effective dosage, e.g., a dosage sufficient to provide treatment for the disease states previously described. Administration can be via any of the accepted modes of administration, i.e., by intravenous infusion or injection, subcutaneously, or intrathecally.

Human approved dosage levels for treatment of acute non-lymphocytic leukemia (in combination with other anti-cancer drugs) are 100 mg/m$^2$ day by continuous IV infusion (Days 1–7) or 100 mg/m$^2$ IV every 12 hours (Days 1–7). For intrathecal use in acute leukemia, doses range from 5 mg/m$^2$ to 75 mg/m$^2$ of body surface area, once every day for 4 days to once every 4 days, preferably 30 mg/m$^2$ every 4 days until CSF findings are normal, followed by one additional treatment.

For the treatment of SLE, ara-C can be administered as described above or preferably, for example, s.q. at 0.5 to 2.5 mg/kg (preferably about 1 to 2.0 mg/kg) for 3 to 7 (preferably about 5) consecutive days (optionally co-administered with ondansetron, e.g., 8 mg p.o. t.i.d.). This is repeated every third or fourth week until disease symptoms remit, and as necessary thereafter in the event of remission.

EXAMPLES

The following preparations and examples are given to enable those skilled in the art to more clearly understand and to practice the present invention. They should not be considered as limiting the scope of the invention, but merely as being illustrative and representative thereof.

EXAMPLE 1 Treatment of SLE

Three female patients were treated using a protocol previously shown to be immunosuppressive in humans (Mitchell et al, *Ann. Intern. Med.*, 70:535–546 (1969). Written consent was obtained in all cases. None of the subjects had significant hematologic abnormalities or impairment of renal function, none were receiving DNA synthesis inhibitors, and all were using effective contraception. Cytarabine was administered s.q. at 2 mg/kg for 5 consecutive days, together with ondansetron 8 mg p.o. t.i.d. This was repeated every fourth week for a total of 3 courses. Clinical assessment (Systemic Lupus Activity Measure) (Liang, et al., *Arthritis Rheum.*, 32:1107–1118 (1989) and routine laboratory monitoring were performed weekly for the first cycle, then every other week for a total of 12 weeks.

Case 1:

K. K. is a 23-year-old woman with SLE for 17 years, manifested by a rash involving the face, hands and upper trunk, photosensitivity, alopecia, oral/nasal ulcerations, arthritis, serositis, fatigue, Raynaud's, leukopenia, hypocomplementemia, positive anti-nuclear antibody (ANA), and autoantibodies to double-stranded DNA and Sm. She had previously been treated with hydroxychloroquine, chloroquine, quinacrine, prednisone, azathioprine, levamisole, methotrexate, cyclophosphamide and nitrogen mustard. A combination of i.v. cyclophosphamide, prednisone 30 mg/d, and antimalarials resulted in mild improvement, but was complicated by retinal pigmentation, cataracts, and avascular necrosis. The other agents were either ineffective or poorly tolerated.

Cytarabine was administered at 2 mg/kg on weeks one, five, and nine. During the second week of each cycle, her rash began to clear, with maximum improvement during the third week, and began to relapse during the fourth week. Improvement in fatigue, Raynaud's, dyspnea, headache and cortical dysfunction were also reported. Her $C_3$ level normalized, and $C_4$ rose from undetectable to borderline low. Therapy was accompanied by asymptomatic mild thrombocytopenia (147,000/mm$^3$) occurring during the second week. A mild leukopenia (3,100/mm$^3$) was observed on one occasion. Because the cutaneous improvement was not sustained, her prednisone was increased from 30 to 40 mg/d during the third course. This, however, did not prolong the response.

Case 2:

C. O. is a 44-year-old woman with lupus for 15 years, manifested by photosensitivity, alopecia, discoid and ulcerative scalp lesions requiring skin grafting in 1988, arthritis, oral ulcerations, fatigue, and a positive ANA and autoantibodies to Ro. Prednisone, quinacrine, chloroquine, azathioprine, and hydroxychloroquine were previously ineffective. Cytarabine was administered as in Case 1. Mild nausea and one episode of emesis accompanied the first course. Her scalp lesions began to improve by the second week, and improved slowly but continuously over the second course of therapy. Improvement in arthritis was also noted. The dose of cytarabine was increased to 3 mg/kg for the third cycle in an attempt to improve the clinical response. This resulted in several episodes of emesis and a diffuse pruritic rash due either to the ondansetron or cytarabine, but no thrombocytopenia or leukopenia. No further increase in efficacy was observed at this dose, and her scalp disease relapsed 4 weeks after the last cycle.

Case 3:

S. H. is a 35-year-old woman with subacute cutaneous lupus for 14 years, manifested by a non-scarring photosensitive rash, arthritis, oral and nasal ulcers, serositis, Raynaud's, fever, fatigue, a positive ANA and autoantibodies to Ro. Prednisone, azathioprine, quinacrine, hydroxychloroquine, dapsone, and sulfapyridine were all either ineffective or poorly tolerated. Cytarabine was administered as above. Dramatic clearing of the skin lesions was observed during the second and third week of therapy, with a tendency to relapse during the fourth week. Because of the transient improvement, her dose was increased to 3 mg/kg/day during the third cycle of therapy. This was complicated by thrombocytopenia (24,000/mm$^3$) and menorrhagia. The platelet count normalized within a week, but the increased dose did not result in prolonged skin improvement.

Conclusion

In these three cases, cytarabine caused a significant response in otherwise refractory cutaneous lupus. The improvement was rapid, but relapsed during the fourth week in two cases. Other disease manifestations also appeared to improve, suggesting cytarabine to be effective for these and other SLE manifestations.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A method of treatment for systemic lupus erythematosus comprising administering to a patient in need thereof an effective amount of cytarabine.

2. The method of treatment of claim 1 wherein the disease is cutaneous systemic lupus erythematosus.

3. The method of treatment of claim 1 wherein the disease is refractory cutaneous lupus erythematosus.

4. The method of treatment of claim 1 comprising administering 1 to 2.0 mg/kg of cytarabine for about 5 consecutive days.

5. The method of treatment of claim 4 wherein treatment is repeated about every third or fourth week.

6. The method of treatment of claim 1 further comprising the co-administration of ondansetron.

7. The method of treatment of claim 1 wherein cytarabine is employed in an accepted treatment regimen as asteroid sparing agent facilitating the use of lower concommittant steroid doses.

8. The method of treatment of claim 7 wherein the steroid prednisone is administered at a lower than typical dosage level.

9. A method of treatment for systemic lupus erythematosus comprising substituting an effective amount of cytarabine in place of azathioprine.

* * * * *